United States Patent [19]
Tarr et al.

[11] Patent Number: 5,654,417
[45] Date of Patent: Aug. 5, 1997

[54] NUCLEIC ACID PROBES FOR DETECTING E. COLI O157:H7

[75] Inventors: Phillip I. Tarr, Seattle; Sima S. Bilge, Bellevue; James C. Vary, Jr., Seattle, all of Wash.

[73] Assignees: Children's Hospital and Medical Center; University of Washington, both of Seattle, Wash.

[21] Appl. No.: 423,564

[22] Filed: Apr. 14, 1995

[51] Int. Cl.⁶ .............................. C07H 21/04; C12Q 1/68
[52] U.S. Cl. ...................... 536/24.32; 435/6; 536/23.1; 536/24.3
[58] Field of Search ................... 435/6; 5365/23.1, 5365/24.3, 24.32

[56] References Cited

U.S. PATENT DOCUMENTS

| | | | |
|---|---|---|---|
| 4,795,805 | 1/1989 | Lindberg et al. | 530/324 |
| 5,475,098 | 12/1995 | Hall et al. | 536/23.7 |

FOREIGN PATENT DOCUMENTS

WO89/12693  12/1989  WIPO.

OTHER PUBLICATIONS

New England Biolabs (1993/1994 Edition) pp. 92–95.
E. coli 0157 Test, Oxoid Diagnostic Reagents, Unipath Limited, Basingstoke, Hampshire, England.
Tarr, Clinical Infectious Diseases, 20:1–8, 1995.
Levine et al., The Journal of Infectious Diseases 156(1):175–182, 1987.
Samadpour et al., Applied and Environmental Microbiology 56(5):1212–1215, 1990.
Pollard et al., Journal of Clinical Microbiology 28(3):540–545, 1990.
Pollard et al., The Journal of Infectious Diseases 162:1195–1198, 1990.
Feng et al., Applied and Environmental Microbiology 57(1):320–323, 1991.
Feng, Molecular and Cellular Probes 7:151–154, 1993.
Cebula et al., Journal of Clinical Microbiology 33(1):248–250, 1995.
Kessler et al., Journal of Bacteriology 175(5):1412–1422, 1993.
Stroeher et al., Proc. Natl. Acad. Sci. USA 89:2566–2570, 1992.
Whittam et al., Infection and Immunity 61:1619–1629, 1993.
Yu et al., Molecular Microbiology 6(3):411–417, 1992.
Beebakhee et al., FEMS Microbiology Letters 91:63–69, 1992.
Guttman et al., Science 266:1380–1383, 1994.

*Primary Examiner*—Stephanie W. Zitomer
*Assistant Examiner*—Ethan Whisenant
*Attorney, Agent, or Firm*—Christensen, O'Connor, Johnson & Kindness PLLC

[57] ABSTRACT

An isolated nucleic acid molecule that hybridizes under stringent conditions to SEQ ID NO:1 or its complement and to the DNA of enterohemorrhagic *E. coli* O157:H7 but not to the DNA of enteropathogenic *E. coli* O55:H7.

2 Claims, No Drawings

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 2255 base pairs
        ( B ) TYPE: nucleic acid
        ( C ) STRANDEDNESS: double
        ( D ) TOPOLOGY: linear ( i i ) MOLECULE TYPE: DNA (genomic)
        ( A ) DESCRIPTION: nucleotide sequence of the F12 region ( i i i ) HYPOTHETICAL: NO ( i v ) ANTI-SENSE: NO ( v i ) ORIGINAL SOURCE:
        ( A ) ORGANISM: Escherichia coli ( x i ) SEQUENCE DESCRIPTION: SEQ ID NO:1:

```
TCGTTTGTCA  TAACTGCAAT  ATGCTATATT  ACTTCTGGCA  TGATTGATTG  GCAACTAGTA      60

ATAAAAGGTA  TAAACGAGAA  TGTGTATGCA  GAGTTACAAC  ACTCAATTAA  AGTCTTTGTA     120

ATCATATTTG  GACTTGGAAT  TTATTCAAAT  GGTGTGCAAA  AAGTTTATAT  GGGAATACAA     180

AAAGCCTATA  TAAGTAATAT  TGTTAATGCC  ATATTTATAT  TGTTATCTAT  TATTACTCTA     240

GTAATATCGT  CGAAACTACA  TGCGGGACTA  CCAGTTTTAA  TTGTCAGCAC  TCTTGGTATT     300

CAATACATAT  CGGGAATCTA  TTTAACAATT  AATCTTATTA  TAAAGCGATT  AATAAAGTTT     360

ACAAAAGTTA  ACATACATGC  TAAAAGAGAA  GCTCCATATT  TGATATTAAA  CGGTTTTTTC     420

TTTTTATTT   TACAGTTAGG  CACTCTGGCA  ACATGGAGTG  GTGATAACTT  TATAATATCT     480

ATAACATTGG  GTGTTACTTA  TGTTGCTGTT  TTTAGCATTA  CACAGAGATT  ATTTCAAATA     540

TCTACGGTCC  CTCTTACGAT  TTATAACATC  CCGTTATGGG  CTGCTTATGC  AGATGCTCAT     600

GCACGCAATG  ATACTCAATT  TATAAAAAAG  ACGCTCAGAA  CATCATTGAA  AATAGTGGGT     660

ATTTCATCAT  TCTTATTGGC  CTTCATATTA  GTAGTGTTCG  GTAGTGAAGT  CGTTAATATT     720

TGGACAGAAG  GAAAGATTCA  GGTACCTCGA  ACATTCATAA  TAGCTTATGC  TTTATGGTCT     780

GTTATTGATG  CTTTTTCGAA  TACATTTGCA  AGCTTTTTAA  ATGGTTTGAA  CATAGTTAAA     840

CAACAAATGC  TTGCTGTTGT  AACATTGATA  TTGATCGCAA  TTCCAGCAAA  ATACATCATA     900

GTTAGCCATT  TTGGGTTAAC  TGTTATGTTG  TACTGCTTCA  TTTTATATA   TATTGTAAAT     960
```

-continued

```
TACCTTATAT GGTATAAATG TAGTTTTAAA AAACATATCG ATAGACAGTT AAATATAAGA    1020
GGATGAAAAT GAAATATATA CCAGTTTACC AACCGTCATT GACAGGAAAA GAAAAGAAT    1080
ATGTAAATGA ATGTCTGGAC TCAACGTGGA TTTCATCAAA AGGAAACTAT ATTCAGAAGT    1140
TTGAAAATAA ATTTGCGGAA CAAAACCATG TGCAATATGC AACTACTGTA AGTAATGGAA    1200
CGGTTGCTCT TCATTTAGCT TTGTTAGCGT TAGGTATATC GGAAGGAGAT GAAGTTATTG    1260
TTCCAACACT GACATATATA GCATCAGTTA ATGCTATAAA ATACACAGGA GCCACCCCCA    1320
TTTTCGTTGA TTCAGATAAT GAAACTTGGC AAATGTCTGT TAGTGACATA GAACAAAAAA    1380
TCACTAATAA AACTAAAGCT ATTATGTGTG TCCATTTATA CGGACATCCA TGTGATATGG    1440
AACAAATTGT AGAACTGGCC AAAAGTAGAA ATTTGTTTGT AATTGAAGAT GCGCTGAAG    1500
CCTTTGGTTT TAAATATAAA GGTAAATATG TGGGAACATT TGGAGATATT TCTACTTTTA    1560
GCTTTTTTGG AAATAAAACT ATTACTACAG GTGAAGGTGG AATGGTTGTC ACGAATGACA    1620
AAACACTTTA TGACCGTTGT TTACATTTTA AAGGCCAAGG ATTAGCTGTA CATAGGCAAT    1680
ATTGGCATGA CGTTATAGGC TACAATTATA GGATGACAAA TATCTGCGCT GCTATAGGAT    1740
TAGCCCAGTT AGAACAAGCT GATGATTTTA TATCACGAAA ACGTGAAATT GCTGATATTT    1800
ATAAAAAAAA TATCAACAGT CTTGTACAAG TCCACAAGGA AAGTAAAGAT GTTTTCACA     1860
CTTATTGGAT GGTCTCAATT CTAACTAGGA CCGCAGAGGA AAGAGAGGAA TTAAGGAATC    1920
ACCTTGCAGA TAAACTCATC GAAACAAGGC CAGTTTTTTA CCCTGTCCAC ACGATGCCAA    1980
TGTACTCGGA AAAATATCAA AAGCACCCTA TAGCTGAGGA TCTTGGTTGG CGTGGAATTA    2040
ATTTACCTAG TTTCCCCAGC CTATCGAATG AGCAAGTTAT TTATATTTGT GAATCTATTA    2100
ACGAATTTTA TAGTGATAAA TAGCCTAAAA TATTGTAAAG GTCATTCATG AAAATTGCGT    2160
TGAATTCAGA TGGATTTTAC GAGTGGGGCG GTGGAATTGA TTTTATTAAA TATATTCTGT    2220
CAATATTAGA AACGAAACCA GAAATATGTA TCGAT                               2255
```

( 2 ) INFORMATION FOR SEQ ID NO:2:

( i ) SEQUENCE CHARACTERISTICS:
        ( A ) LENGTH: 1026 base pairs
        ( B ) TYPE: nucleic acid
        ( C ) STRANDEDNESS: double
        ( D ) TOPOLOGY: linear ( i i ) MOLECULE TYPE: DNA (genomic)
        ( A ) DESCRIPTION: nucleotides 1-1026 of SEQ ID NO:1

( i i i ) HYPOTHETICAL: NO ( i v ) ANTI-SENSE: NO ( v i ) ORIGINAL SOURCE:
        ( A ) ORGANISM: Escherichia coli ( x i ) SEQUENCE DESCRIPTION: SEQ ID NO:2:

```
TCGTTTGTCA TAACTGCAAT ATGCTATATT ACTTCTGGCA TGATTGATTG GCAACTAGTA     60
ATAAAAGGTA TAAACGAGAA TGTGTATGCA GAGTTACAAC ACTCAATTAA AGTCTTTGTA    120
ATCATATTTG GACTTGGAAT TTATTCAAAT GGTGTGCAAA AAGTTTATAT GGGAATACAA    180
AAAGCCTATA TAAGTAATAT TGTTAATGCC ATATTTATAT TGTTATCTAT TATTACTCTA    240
GTAATATCGT CGAAACTACA TGCGGGACTA CCAGTTTTAA TTGTCAGCAC TCTTGGTATT    300
CAATACATAT CGGGAATCTA TTTAACAATT AATCTTATTA TAAAGCGATT AATAAAGTTT    360
ACAAAAGTTA ACATACATGC TAAAAGAGAA GCTCCATATT TGATATTAAA CGGTTTTTTC    420
```

-continued

| | | | | | |
|---|---|---|---|---|---|
| TTTTTTATTT | TACAGTTAGG | CACTCTGGCA | ACATGGAGTG | GTGATAACTT | TATAATATCT | 480 |
| ATAACATTGG | GTGTTACTTA | TGTTGCTGTT | TTTAGCATTA | CACAGAGATT | ATTTCAAATA | 540 |
| TCTACGGTCC | CTCTTACGAT | TTATAACATC | CCGTTATGGG | CTGCTTATGC | AGATGCTCAT | 600 |
| GCACGCAATG | ATACTCAATT | TATAAAAAAG | ACGCTCAGAA | CATCATTGAA | AATAGTGGGT | 660 |
| ATTTCATCAT | TCTTATTGGC | CTTCATATTA | GTAGTGTTCG | GTAGTGAAGT | CGTTAATATT | 720 |
| TGGACAGAAG | GAAAGATTCA | GGTACCTCGA | ACATTCATAA | TAGCTTATGC | TTTATGGTCT | 780 |
| GTTATTGATG | CTTTTTCGAA | TACATTTGCA | AGCTTTTTAA | ATGGTTTGAA | CATAGTTAAA | 840 |
| CAACAAATGC | TTGCTGTTGT | AACATTGATA | TTGATCGCAA | TTCCAGCAAA | ATACATCATA | 900 |
| GTTAGCCATT | TTGGGTTAAC | TGTTATGTTG | TACTGCTTCA | TTTTTATATA | TATTGTAAAT | 960 |
| TACCTTATAT | GGTATAAATG | TAGTTTTAAA | AAACATATCG | ATAGACAGTT | AAATATAAGA | 1020 |
| GGATGA | | | | | | 1026 |

( 2 ) INFORMATION FOR SEQ ID NO:3:

( i ) SEQUENCE CHARACTERISTICS:
        ( A ) LENGTH: 1095 base pairs
        ( B ) TYPE: nucleic acid
        ( C ) STRANDEDNESS: double
        ( D ) TOPOLOGY: linear ( i i ) MOLECULE TYPE: DNA (genomic)
        ( A ) DESCRIPTION: nucleotides 1029- 2123 of SEQ ID NO:1

( i i i ) HYPOTHETICAL: NO ( i v ) ANTI-SENSE: NO ( v i ) ORIGINAL SOURCE:
        ( A ) ORGANISM: Escherichia coli ( x i ) SEQUENCE DESCRIPTION: SEQ ID NO:3:

| | | | | | |
|---|---|---|---|---|---|
| ATGAAATATA | TACCAGTTTA | CCAACCGTCA | TTGACAGGAA | AAGAAAAAGA | ATATGTAAAT | 60 |
| GAATGTCTGG | ACTCAACGTG | GATTTCATCA | AAAGGAAACT | ATATTCAGAA | GTTTGAAAAT | 120 |
| AAATTTGCGG | AACAAAACCA | TGTGCAATAT | GCAACTACTG | TAAGTAATGG | AACGGTTGCT | 180 |
| CTTCATTTAG | CTTTGTTAGC | GTTAGGTATA | TCGGAAGGAG | ATGAAGTTAT | TGTTCCAACA | 240 |
| CTGACATATA | TAGCATCAGT | TAATGCTATA | AAATACACAG | GAGCCACCCC | CATTTTCGTT | 300 |
| GATTCAGATA | ATGAAACTTG | GCAAATGTCT | GTTAGTGACA | TAGAACAAAA | AATCACTAAT | 360 |
| AAAACTAAAG | CTATTATGTG | TGTCCATTTA | TACGGACATC | CATGTGATAT | GGAACAAATT | 420 |
| GTAGAACTGG | CCAAAAGTAG | AAATTTGTTT | GTAATTGAAG | ATTGCGCTGA | AGCCTTTGGT | 480 |
| TTTAAATATA | AAGGTAAATA | TGTGGGAACA | TTTGGAGATA | TTTCTACTTT | TAGCTTTTTT | 540 |
| GGAAATAAAA | CTATTACTAC | AGGTGAAGGT | GGAATGGTTG | TCACGAATGA | CAAAACACTT | 600 |
| TATGACCGTT | GTTTACATTT | TAAAGGCCAA | GGATTAGCTG | TACATAGGCA | ATATTGGCAT | 660 |
| GACGTTATAG | GCTACAATTA | TAGGATGACA | AATATCTGCG | CTGCTATAGG | ATTAGCCCAG | 720 |
| TTAGAACAAG | CTGATGATTT | TATATCACGA | AAACGTGAAA | TTGCTGATAT | TTATAAAAAA | 780 |
| AATATCAACA | GTCTTGTACA | AGTCCACAAG | GAAAGTAAAG | ATGTTTTTCA | CACTTATTGG | 840 |
| ATGGTCTCAA | TTCTAACTAG | GACCGCAGAG | GAAAGAGAGG | AATTAAGGAA | TCACCTTGCA | 900 |
| GATAAACTCA | TCGAAACAAG | GCCAGTTTTT | TACCCTGTCC | ACACGATGCC | AATGTACTCG | 960 |
| GAAAAATATC | AAAAGCACCC | TATAGCTGAG | GATCTTGGTT | GGCGTGGAAT | TAATTTACCT | 1020 |
| AGTTTCCCCA | GCCTATCGAA | TGAGCAAGTT | ATTTATATTT | GTGAATCTAT | TAACGAATTT | 1080 |
| TATAGTGATA | AATAG | | | | | 1095 |

5,654,417

13

-continued

14

( 2 ) INFORMATION FOR SEQ ID NO:4:

( i ) SEQUENCE CHARACTERISTICS:
  ( A ) LENGTH: 1287 base pairs
  ( B ) TYPE: nucleic acid
  ( C ) STRANDEDNESS: double
  ( D ) TOPOLOGY: linear ( i i ) MOLECULE TYPE: DNA (genomic)
  ( A ) DESCRIPTION: nucleotides 913- 2199 of SEQ ID NO:1

( i i i ) HYPOTHETICAL: NO ( i v ) ANTI-SENSE: NO ( v i ) ORIGINAL SOURCE:
  ( A ) ORGANISM: Escherichia coli ( x i ) SEQUENCE DESCRIPTION: SEQ ID NO:4:

| | | | | | | |
|---|---|---|---|---|---|---|
| GGGTTAACTG | TTATGTTGTA | CTGCTTCATT | TTTATATATA | TTGTAAATTA | CCTTATATGG | 60 |
| TATAAATGTA | GTTTTAAAAA | ACATATCGAT | AGACAGTTAA | ATATAAGAGG | ATGAAAATGA | 120 |
| AATATATACC | AGTTTACCAA | CCGTCATTGA | CAGGAAAAGA | AAAAGAATAT | GTAAATGAAT | 180 |
| GTCTGGACTC | AACGTGGATT | TCATCAAAAG | GAAACTATAT | TCAGAAGTTT | GAAAATAAAT | 240 |
| TTGCGGAACA | AAACCATGTG | CAATATGCAA | CTACTGTAAG | TAATGGAACG | GTTGCTCTTC | 300 |
| ATTTAGCTTT | GTTAGCGTTA | GGTATATCGG | AAGGAGATGA | AGTTATTGTT | CCAACACTGA | 360 |
| CATATATAGC | ATCAGTTAAT | GCTATAAAAT | ACACAGGAGC | CACCCCCATT | TTCGTTGATT | 420 |
| CAGATAATGA | AACTTGGCAA | ATGTCTGTTA | GTGACATAGA | ACAAAAAATC | ACTAATAAAA | 480 |
| CTAAAGCTAT | TATGTGTGTC | CATTTATACG | GACATCCATG | TGATATGGAA | CAAATTGTAG | 540 |
| AACTGGCCAA | AAGTAGAAAT | TTGTTTGTAA | TTGAAGATTG | CGCTGAAGCC | TTTGGTTTTA | 600 |
| AATATAAAGG | TAAATATGTG | GGAACATTTG | GAGATATTTC | TACTTTTAGC | TTTTTTGGAA | 660 |
| ATAAAACTAT | TACTACAGGT | GAAGGTGGAA | TGGTTGTCAC | GAATGACAAA | ACACTTTATG | 720 |
| ACCGTTGTTT | ACATTTTAAA | GGCCAAGGAT | TAGCTGTACA | TAGGCAATAT | TGGCATGACG | 780 |
| TTATAGGCTA | CAATTATAGG | ATGACAAATA | TCTGCGCTGC | TATAGGATTA | GCCCAGTTAG | 840 |
| AACAAGCTGA | TGATTTTATA | TCACGAAAAC | GTGAAATTGC | TGATATTTAT | AAAAAAAATA | 900 |
| TCAACAGTCT | TGTACAAGTC | CACAAGGAAA | GTAAAGATGT | TTTTCACACT | TATTGGATGG | 960 |
| TCTCAATTCT | AACTAGGACC | GCAGAGGAAA | GAGAGGAATT | AAGGAATCAC | CTTGCAGATA | 1020 |
| AACTCATCGA | AACAAGGCCA | GTTTTTTACC | CTGTCCACAC | GATGCCAATG | TACTCGGAAA | 1080 |
| AATATCAAAA | GCACCCTATA | GCTGAGGATC | TTGGTTGGCG | TGGAATTAAT | TTACCTAGTT | 1140 |
| TCCCCAGCCT | ATCGAATGAG | CAAGTTATTT | ATATTTGTGA | ATCTATTAAC | GAATTTTATA | 1200 |
| GTGATAAATA | GCCTAAAATA | TTGTAAAGGT | CATTCATGAA | AATTGCGTTG | AATTCAGATG | 1260 |
| GATTTTACGA | GTGGGGCGGT | GGAATTG | | | | 1287 |

( 2 ) INFORMATION FOR SEQ ID NO:5:

( i ) SEQUENCE CHARACTERISTICS:
  ( A ) LENGTH: 341 amino acids
  ( B ) TYPE: amino acid
  ( C ) STRANDEDNESS: single
  ( D ) TOPOLOGY: linear ( i i ) MOLECULE TYPE: protein
  ( A ) DESCRIPTION: amino acids encoded by
   nucleotides 1-1026 of SEQ ID NO:1

( i i i ) HYPOTHETICAL: NO (iv) ANTI-SENSE: NO (vi) ORIGINAL SOURCE:
 (A) ORGANISM: Escherichia coli (xi) SEQUENCE DESCRIPTION: SEQ ID NO:5:

```
Ser Phe Val Ile Thr Ala Ile Cys Tyr Ile Thr Ser Gly Met Ile Asp
1               5                   10                  15

Trp Gln Leu Val Ile Lys Gly Ile Asn Glu Asn Val Tyr Ala Glu Leu
            20                  25                  30

Gln His Ser Ile Lys Val Phe Val Ile Ile Phe Gly Leu Gly Ile Tyr
        35              40                      45

Ser Asn Gly Val Gln Lys Val Tyr Met Gly Ile Gln Lys Ala Tyr Ile
    50              55                      60

Ser Asn Ile Val Asn Ala Ile Phe Ile Leu Leu Ser Ile Ile Thr Leu
65              70                  75                      80

Val Ile Ser Ser Lys Leu His Ala Gly Leu Pro Val Leu Ile Val Ser
                85                  90                  95

Thr Leu Gly Ile Gln Tyr Ile Ser Gly Ile Tyr Leu Thr Ile Asn Leu
            100                 105                 110

Ile Ile Lys Arg Leu Ile Lys Phe Thr Lys Val Asn Ile His Ala Lys
        115             120                 125

Arg Glu Ala Pro Tyr Leu Ile Leu Asn Gly Phe Phe Phe Ile Leu
    130             135                 140

Gln Leu Gly Thr Leu Ala Thr Trp Ser Gly Asp Asn Phe Ile Ile Ser
145                 150                 155                 160

Ile Thr Leu Gly Val Thr Tyr Val Ala Val Phe Ser Ile Thr Gln Arg
                165                 170                 175

Leu Phe Gln Ile Ser Thr Val Pro Leu Thr Ile Tyr Asn Ile Pro Leu
            180                 185                 190

Trp Ala Ala Tyr Ala Asp Ala His Ala Arg Asn Asp Thr Gln Phe Ile
        195                 200                 205

Lys Lys Thr Leu Arg Thr Ser Leu Lys Ile Val Gly Ile Ser Ser Phe
    210                 215                 220

Leu Leu Ala Phe Ile Leu Val Val Phe Gly Ser Glu Val Val Asn Ile
225                 230                 235                 240

Trp Thr Glu Gly Lys Ile Gln Val Pro Arg Thr Phe Ile Ile Ala Tyr
                245                 250                 255

Ala Leu Trp Ser Val Ile Asp Ala Phe Ser Asn Thr Phe Ala Ser Phe
            260                 265                 270

Leu Asn Gly Leu Asn Ile Val Lys Gln Gln Met Leu Ala Val Val Thr
        275                 280                 285

Leu Ile Leu Ile Ala Ile Pro Ala Lys Tyr Ile Ile Val Ser His Phe
    290                 295                 300

Gly Leu Thr Val Met Leu Tyr Cys Phe Ile Phe Ile Tyr Ile Val Asn
305                 310                 315                 320

Tyr Phe Ile Trp Tyr Lys Cys Ser Phe Lys Lys His Ile Asp Arg Gln
                325                 330                 335

Leu Asn Ile Arg Gly
                340
```

(2) INFORMATION FOR SEQ ID NO:6:

(i) SEQUENCE CHARACTERISTICS:
  (A) LENGTH: 364 amino acids
  (B) TYPE: amino acid (C) STRANDEDNESS: double
(D) TOPOLOGY: linear (ii) MOLECULE TYPE: protein
    (A) DESCRIPTION: amino acids encoded by
        nucleotides 1029-2123 of SEQ ID NO:1

(iii) HYPOTHETICAL: NO (iv) ANTI-SENSE: NO (vi) ORIGINAL SOURCE:
    (A) ORGANISM: Escherichia coli (xi) SEQUENCE DESCRIPTION: SEQ ID NO:6:

```
Met Lys Tyr Ile Pro Val Tyr Gln Pro Ser Leu Thr Gly Lys Glu Lys
 1               5                  10                  15

Glu Tyr Val Asn Glu Cys Leu Asp Ser Thr Trp Ile Ser Ser Lys Gly
                20                  25                  30

Asn Tyr Ile Gln Lys Phe Glu Asn Lys Phe Ala Glu Gln Asn His Val
            35                  40                  45

Gln Tyr Ala Thr Thr Val Ser Asn Gly Thr Val Ala Leu His Leu Ala
        50                  55                  60

Leu Leu Ala Leu Gly Ile Ser Glu Gly Asp Glu Val Ile Val Pro Thr
65                  70                  75                  80

Leu Thr Tyr Ile Ala Ser Val Asn Ala Ile Lys Tyr Thr Gly Ala Thr
                85                  90                  95

Pro Ile Phe Val Asp Ser Asp Asn Glu Thr Trp Gln Met Ser Val Ser
               100                 105                 110

Asp Ile Glu Gln Lys Ile Thr Asn Lys Thr Lys Ala Ile Met Cys Val
           115                 120                 125

His Leu Tyr Gly His Pro Cys Asp Met Glu Gln Ile Val Glu Leu Ala
       130                 135                 140

Lys Ser Arg Asn Leu Phe Val Ile Glu Asp Cys Ala Glu Ala Phe Gly
145                 150                 155                 160

Ser Lys Tyr Lys Gly Lys Tyr Val Gly Thr Phe Gly Asp Ile Ser Thr
                165                 170                 175

Phe Ser Phe Phe Gly Asn Lys Thr Ile Thr Thr Gly Glu Gly Gly Met
            180                 185                 190

Val Val Thr Asn Asp Lys Thr Leu Tyr Asp Arg Cys Leu His Phe Lys
        195                 200                 205

Gly Gln Gly Leu Ala Val His Arg Gln Tyr Trp His Asp Val Ile Gly
210                 215                 220

Tyr Asn Tyr Arg Met Thr Asn Ile Cys Ala Ala Ile Gly Leu Ala Gln
225                 230                 235                 240

Leu Glu Gln Ala Asp Asp Phe Ile Ser Arg Lys Arg Glu Ile Ala Asp
                245                 250                 255

Ile Tyr Lys Lys Asn Ile Asn Ser Leu Val Gln Val His Lys Glu Ser
            260                 265                 270

Lys Asp Val Phe His Thr Tyr Trp Met Val Ser Ile Leu Thr Arg Thr
        275                 280                 285

Ala Glu Glu Arg Glu Glu Leu Arg Asn His Leu Ala Asp Lys Leu Ile
290                 295                 300

Glu Thr Arg Pro Val Phe Tyr Pro Val His Thr Met Pro Met Tyr Ser
305                 310                 315                 320

Glu Lys Tyr Gln Lys His Pro Ile Ala Glu Asp Leu Gly Trp Arg Gly
                325                 330                 335

Ile Asn Leu Pro Ser Phe Pro Ser Leu Ser Asn Glu Gln Val Ile Tyr
```

|   | 340 |   | 345 |   | 350 |
|---|---|---|---|---|---|

Ile Cys Glu Ser Ile Asn Glu Phe Tyr Ser Asp Lys
              355              360

( 2 ) INFORMATION FOR SEQ ID NO:7:

( i ) SEQUENCE CHARACTERISTICS:
        ( A ) LENGTH: 2168 base pairs
        ( B ) TYPE: nucleic acid
        ( C ) STRANDEDNESS: double
        ( D ) TOPOLOGY: linear ( i i ) MOLECULE TYPE: DNA (genomic)
        ( A ) DESCRIPTION: nucleotides 32-2199 of SEQ ID NO:1

( i i i ) HYPOTHETICAL: NO ( i v ) ANTI-SENSE: NO ( v i ) ORIGINAL SOURCE:
        ( A ) ORGANISM: Escherichia coli ( x i ) SEQUENCE DESCRIPTION: SEQ ID NO:7:

```
CTTCTGGCAT GATTGATTGG CAACTAGTAA TAAAAGGTAT AAACGAGAAT GTGTATGCAG        60
AGTTACAACA CTCAATTAAA GTCTTTGTAA TCATATTTGG ACTTGGAATT TATTCAAATG       120
GTGTGCAAAA AGTTTATATG GGAATACAAA AAGCCTATAT AAGTAATATT GTTAATGCCA       180
TATTTATATT GTTATCTATT ATTACTCTAG TAATATCGTC GAAACTACAT GCGGGACTAC       240
CAGTTTTAAT TGTCAGCACT CTTGGTATTC AATACATATC GGGAATCTAT TTAACAATTA       300
ATCTTATTAT AAAGCGATTA ATAAAGTTTA CAAAGTTAA CATACATGCT AAAAGAGAAG        360
CTCCATATTT GATATTAAAC GGTTTTTTCT TTTTTATTTT ACAGTTAGGC ACTCTGGCAA       420
CATGGAGTGG TGATAACTTT ATAATATCTA TAACATTGGG TGTTACTTAT GTTGCTGTTT       480
TTAGCATTAC ACAGAGATTA TTTCAAATAT CTACGGTCCC TCTTACGATT TATAACATCC       540
CGTTATGGGC TGCTTATGCA GATGCTCATG CACGCAATGA TACTCAATTT ATAAAAAGA       600
CGCTCAGAAC ATCATTGAAA ATAGTGGGTA TTTCATCATT CTTATTGGCC TTCATATTAG       660
TAGTGTTCGG TAGTGAAGTC GTTAATATTT GGACAGAAGG AAAGATTCAG GTACCTCGAA       720
CATTCATAAT AGCTTATGCT TTATGGTCTG TTATTGATGC TTTTCGAAT ACATTTGCAA        780
GCTTTTAAA TGGTTTGAAC ATAGTTAAAC AACAAATGCT TGCTGTTGTA ACATTGATAT        840
TGATCGCAAT TCCAGCAAAA TACATCATAG TTAGCCATTT TGGGTTAACT GTTATGTTGT       900
ACTGCTTCAT TTTTATATAT ATTGTAAATT ACCTTATATG GTATAAATGT AGTTTAAAA        960
AACATATCGA TAGACAGTTA AATATAAGAG GATGAAAATG AAATATATAC CAGTTTACCA      1020
ACCGTCATTG ACAGGAAAAG AAAAAGAATA TGTAAATGAA TGTCTGGACT CAACGTGGAT      1080
TTCATCAAAA GGAAACTATA TTCAGAAGTT TGAAAATAAA TTTGCGGAAC AAAACCATGT      1140
GCAATATGCA ACTACTGTAA GTAATGGAAC GGTTGCTCTT CATTTAGCTT TGTTAGCGTT      1200
AGGTATATCG GAAGGAGATG AAGTTATTGT TCCAACACTG ACATATATAG CATCAGTTAA      1260
TGCTATAAAA TACACAGGAG CCACCCCCAT TTTCGTTGAT TCAGATAATG AAACTTGGCA      1320
AATGTCTGTT AGTGACATAG AACAAAAAAT CACTAATAAA ACTAAAGCTA TTATGTGTGT      1380
CCATTTATAC GGACATCCAT GTGATATGGA ACAAATTGTA GAACTGGCCA AAGTAGAAA       1440
TTTGTTTGTA ATTGAAGATT GCGCTGAAGC CTTTGGTTTT AAATATAAAG GTAAATATGT      1500
GGGAACATTT GGAGATATTT CTACTTTTAG CTTTTTTGGA AATAAAACTA TTACTACAGG      1560
TGAAGGTGGA ATGGTTGTCA CGAATGACAA AACACTTTAT GACCGTTGTT TACATTTTAA      1620
```

| | | | | | | |
|---|---|---|---|---|---|---|
| AGGCCAAGGA | TTAGCTGTAC | ATAGGCAATA | TTGGCATGAC | GTTATAGGCT | ACAATTATAG | 1680 |
| GATGACAAAT | ATCTGCGCTG | CTATAGGATT | AGCCCAGTTA | GAACAAGCTG | ATGATTTAT | 1740 |
| ATCACGAAAA | CGTGAAATTG | CTGATATTTA | TAAAAAAAAT | ATCAACAGTC | TTGTACAAGT | 1800 |
| CCACAAGGAA | AGTAAAGATG | TTTTTCACAC | TTATTGGATG | GTCTCAATTC | TAACTAGGAC | 1860 |
| CGCAGAGGAA | AGAGAGGAAT | TAAGGAATCA | CCTTGCAGAT | AAACTCATCG | AAACAAGGCC | 1920 |
| AGTTTTTTAC | CCTGTCCACA | CGATGCCAAT | GTACTCGGAA | AAATATCAAA | AGCACCCTAT | 1980 |
| AGCTGAGGAT | CTTGGTTGGC | GTGGAATTAA | TTTACCTAGT | TTCCCCAGCC | TATCGAATGA | 2040 |
| GCAAGTTATT | TATATTTGTG | AATCTATTAA | CGAATTTTAT | AGTGATAAAT | AGCCTAAAAT | 2100 |
| ATTGTAAAGG | TCATTCATGA | AAATTGCGTT | GAATTCAGAT | GGATTTACG | AGTGGGGCGG | 2160 |
| TGGAATTG | | | | | | 2168 |

(2) INFORMATION FOR SEQ ID NO:8:

(i) SEQUENCE CHARACTERISTICS:
        (A) LENGTH: 21 bases
        (B) TYPE: nucleic acid
        (C) STRANDEDNESS: single
        (D) TOPOLOGY: linear (ii) MOLECULE TYPE: DNA (genomic)
        (A) DESCRIPTION: nucleotides 32-52 of SEQ ID NO:1

(iii) HYPOTHETICAL: NO (iv) ANTI-SENSE: NO (vi) ORIGINAL SOURCE:
        (A) ORGANISM: Escherichia coli (xi) SEQUENCE DESCRIPTION: SEQ ID NO:8:

CTTCTGGCAT GATTGATTGG C        21

(2) INFORMATION FOR SEQ ID NO:9:

(i) SEQUENCE CHARACTERISTICS:
        (A) LENGTH: 20 bases
        (B) TYPE: nucleic acid
        (C) STRANDEDNESS: single
        (D) TOPOLOGY: linear (ii) MOLECULE TYPE: DNA (genomic)
        (A) DESCRIPTION: nucleotides 2180- 2199 of SEQ ID NO:1

(iii) HYPOTHETICAL: NO (iv) ANTI-SENSE: NO (vi) ORIGINAL SOURCE:
        (A) ORGANISM: Escherichia coli (xi) SEQUENCE DESCRIPTION: SEQ ID NO:9:

CGAGTGGGGC GGTGGAATTG        20

NUCLEIC ACID PROBES FOR DETECTING E. COLI O157:H7

FIELD OF THE INVENTION

The invention relates to genetic engineering and provides nucleic acid probes for detecting pathogenic *Escherichia coli* O157:H7 in food and fecal samples.

BACKGROUND OF THE INVENTION

*E. coli* O157:H7 is a virulent food-borne pathogen that causes acute hemorrhagic colitis (bloody inflammation of the colon), and sometimes a severe hemolytic uremic syndrome (HUS), in children. These conditions can be fatal, or cause permanent kidney damage and shortened life expectancy. Treatment options for this infection are limited; prevention of human infection is therefore of the greatest importance.

Epidemics of *E. coli* O157:H7 generally have been traced to contaminated water or meats, especially undercooked hamburger. Following the 1993 massive outbreak in Washington State, the strain responsible for the epidemic disappeared soon after the recall of the incriminated vehicle. Hence, ingestion of contaminated beef, and not person to person spread, appears to be the chief source of human infection.

Because of the rapid onset of life-threatening complications, expedient diagnosis is of utmost importance to those infected with this strain of *E. coli*, especially when the patient is a child. However, because the early symptoms of this disease can mimic other disorders, patients infected with this organism during the initial stages of new epidemics may not be tested for *E. coli* O157:H7 until other causes have been ruled out. Once *E. coli* O157:H7 is suspected, diagnostic testing methods currently available require about a day to complete before a definitive diagnosis can be confirmed. Any means for shortening this dangerous delay would reduce the risk to infected patients and family members who might become infected through person to person transmission.

Of utmost importance for controlling outbreaks of *E. coli* O157:H7 is the rapid detection of the contaminated food source. A common method for detecting *E. coli* O157:H7 includes incubation on agar containing sorbitol, a substrate that supports growth of most fecal *E. coli* strains, but which the O157:H7 strain cannot metabolize. However, failure to ferment sorbitol does not provide a definitive diagnosis, as non-pathogenic strains of *E. coli* exist that also cannot ferment sorbitol.

A latex agglutination test for identification of the serogroup O157 is available from Oxoid (Unipath Limited, Basingstoke, Hampshire, England), which recommends that the test be applied to isolates that already have been determined to lack the ability to ferment sorbitol. This antibody-based test lacks specificity: Some strains of *E. hermnaii* share the antigen detected by the antiserum; hence this test must be confirmed by further fermentation testing before an isolate can be conclusively identified as *E. coli* O157:H7. Furthermore, noncytotoxic *E. coli* may possess the *E. coli* O157 antigen, leading to false positive reactions in such O157 antigen detection systems.

Other diagnostic methods for *E. coli* O157:H7 have been suggested. Immunofluorescent examination of fresh stool with labeled O157-specific antiserum has recently been proposed as a rapid technique for the detection of patients whose stools contain *E. coli* O157:H7 (Park et al., Am. J. Clin. Path. 101:91–94, 1994). Antibody-coated magnetic beads (Dynal) are available that react with *E. coli* O157:H7 However, antigen detection tests should be accompanied by a confirmatory stool culture (Tarr, Clinical Infectious Diseases, 20:1–8, 1995).

A test kit for *E. coli* O157:H7 is available which reportedly can detect this organism in meat (Organon Teknika, Durham, N.C.). This is an antigen-based technology, in which bacterial antigens are used as targets to identify the organism. The test requires a day (i.e., overnight) to produce a presumptive positive test. An additional technique which has been proposed is based on a rapid dipstick immunoassay to detect enterohemorrhagic *E. coli* O157:H7 in retail ground beef (Kim et al., Applied Environmental Micobiology 58: 1764–1767, 1992).

For diagnostic purposes, conventional microbiological and antibody-based testing techniques may be insufficient for management of epidemic outbursts of HUS. By the time HUS appears, about two-thirds of patients no longer have *E. coli* O157:H7 in their stools. Moreover, the numbers of organisms present in contaminated food samples often are too low to be readily detected. DNA probes specific for this pathogen would provide an alternative method that is capable of detecting small numbers of organisms. Most efforts in the past to develop such probes have focused on the gene encoding the Shiga-like toxins (SLTs) believed to be responsible for many of strain O157's pathogenic effects. See: Levine et at., The Journal of infectious Diseases 156 (1):175–182, 1987; Samadpour et al., Applied and Environmental Microbiology 56(5):1212–1215, 1990; Pollard et al., Journal of Clinical Microbiology 28(3):540–545, 1990; Pollard et al., The Journal of Infectious Diseases 162:1195–1198, 1990. However, the pathogenecity of many strains containing SLT genes is questionable (Tarr, Clinical Infectious Diseases, 20:1–8, 1995).

PCR assays to detect O157:H7 strains using the uidA gene have also been reported (Feng et at., Applied and Environmental Microbiology 57(1):320–323, 1991; Feng, Molecular and Cellular Probes 7:151–154, 1993.).

More recently, a multiplex PCR assay was reported which uses three sets of primers, two of which are directed to conserved regions within genes encoding for SLT-I and SLT-II, and the third set directed to the uidA gene (Cebula et at., Journal of Clinical Microbiology 33(1):248–250, 1995).

SUMMARY OF THE INVENTION

The invention provides a nucleic acid probe for detecting the presence of enterohemorrhagic *E. coli* O157:H7, comprising an isolated nucleic acid molecule that hybridizes under stringent conditions to SEQ ID NO:1 or its complement and to the DNA of *E. coli* O157:H7 but not to the DNA of the clonally related enteropathogenic *E. coli* O55:H7.

DETAILED DESCRIPTION OF THE PREFERRED EMBODIMENT

The invention provides a DNA fragment (SEQ ID NO:1) that is useful for detecting *E. coli* O157:H7 in food and fecal samples. This DNA fragment, isolated from *E. coli* O157:H7, does not cross-hybridize with the known genes for Shiga toxins in *Shigella dysenteriae*, or the uidA gene which encodes for β-glucoronidase in *E. coli*. Rather, this DNA fragment unexpectedly contains two genes that are related by homology to the putative transmembrane export protein of *Yersinia pseudotuberculosis* (Kessler et al., Journal of Bacteriology 175(5):1412–1422, 1993), and to the rfbE gene which reportedly encodes perosamine synthetase in *Vibrio cholerae* (Stroeher et ai,, Proc. Natl. Acad. Sci, U.S.A. 89:2566–2570, 1992).

The subject DNA fragment was serendipitously identified through efforts to determine the role of the O157 lipopolysaccharide in the pathogenesis of *E. coli* O157:H7. Briefly summarized, TnphoA insertion mutagenesis was used to create mutants of *E. coli* O157:H7 that did not express this antigen. It was noted that such mutants were hyperadherent, that is, they had a pronounced increase in their ability to adhere to HeLa cells. Two O157-hyperadherent mutants, designated 20D2B and F12, were selected for detailed analysis after screening ca. 3000 TnphoA mutants of *E. coil* O157:H7 for the loss of the antigen by the latex particle agglutination test. Both mutant strains were approximately eight-fold more adherent to HeLa cells than the parent strain. Southern blots indicated that these mutants contained two and one TnphoA insertions, respectively. Nucleotide sequence analysis of the DNA regions flanking the F12 insertion surprisingly revealed two open reading frames that share significant homology with the putative transmembrane export protein of *Yersinia pseudotuberculosis* and the rfbE gene of *Vibrio cholerae*. Using PCR primers (identified below) from these flanking regions, the subject DNA fragment was cloned from *E. coil* O157:H7. This fragment is referred to herein as "the F12 region" and its nucleotide sequence is depicted in SEQ ID NO:1.

The invention provides nucleic acid probes derived from the F12 region. Preferred probes are selected from the two open reading flames corresponding to nucleotides 1–1026 (SEQ ID NO:2) and nucleotides 1029–2123 (SEQ ID NO:3) shown in SEQ ID NO:1. By way of example, use of a nucleic acid probe (SEQ ID NO:4), corresponding to nucleotides 913–2199 shown in SEQ ID NO:1, is described below. Other nucleic acid probes can be readily selected from among the contiguous nucleotides within the disclosed sequence(s) and screened for both sensitivity (for strain O157:H7) and specificity (lack of sensitivity for other microbial contaminants of food and feces) using an appropriate panel of positive and negative genomic controls.

In the screening assay, *E. coli* O157:H7 serves as the positive genomic control. Negative genomic controls are selected from among other microbial strains that typically contaminate the type of food, agricultural, or clinical sample to be tested. Such negative genomic controls are preferably selected from among *E. coli* strains that are genetically and antigenically related and most preferably clonally related to strain O157:H7. The clonal relationships among *E. coli* strains that cause hemorrhagic colitis and infantile diarrhea are described in Whittam et al., Infection and Immunity 61:1619–1629, 1993. FIG. 4 therein presents a phylogenetic tree of genomically dosely related strains. In the same lineage as strain O157:H7 are the following clonally related strains which can serve as suitable negative controls, notably: the enteropathogenic strains O55:H7 (i.e., the dosest phylogenetically related strain), O111:H12, and O55:H6. Other *E. coli* strains suitable as negative controls include noncytotoxic and cytotoxic *E. coli* of serotypes O157:H43, O111:H8, O26:H11, O128:H7, O128:H21, O111:H21, O128:H2, and O111:H2.

Bacterial strains for use in the screening panel can be obtained from the reference collections of: the Centers for Disease Control (CDC), Atlanta, Ga.; the *E. coli* Reference Center, University Park, Pa.; the American Type Culture Collection (ATCC), Rockville, Md.; the Center for Vaccine Development, Baltimore, Md.; the Division of Microbiology, Food and Drug Administration (FDA), Washington, D.C.; the Center for Disease Control, Ottawa, Canada; the Universitats-Krankenhaus, Hamburg, Germany; and the Statens Seruminstitut, Copenhagen, Denmark.

Such a reference panel of bacteria can be employed to identify nucleic acid probes from the F12 region shown in SEQ ID NO:1 that provide the requisite sensitivity and selectivity for distinguishing *E. coli* O157:H7 from other bacteria, including related strains of *E. coli*. In a representative screening system, bacteria in the test panel are plated on trypticase soy agar, as described in Samadpour et at., 1990, which is hereby incorporated by reference. Candidate oligonucleotide probes randomly chosen from contiguous nucleotides within the F12 region are synthesized using a DNA synthesizer, following the procedures recommended by the manufacturer. A probe corresponding to SEQ ID NO:4, which has been shown to possess the requisite specificity, may be used as a control probe. All probes are labeled using conventional techniques. Aliquots of chromosomal DNA extracted from each strain of bacteria in the panel are hybridized under stringent conditions with the labeled candidate and control probes. Wild-type *E. coli* O157:H7 serves as the positive control. Candidate probes that hybridize under stringent conditions with O157:H7 but only slightly or not at all with the negative control strains are deemed to have the requisite specificity for detecting *E. coli* O157:H7 in samples of ground meat, bovine feces, and samples of clinical interest.

The F12 fragment (SEQ ID NO:1) can also be employed to identify nucleic acid probes from the *E. coli* O157:H7 genome flanking the F12 region that provide the requisite sensitivity and selectivity. To identify these contiguous sequences using the F12 region, a library of random DNA fragments is generated by partial endonuclease digestion, cloned into an appropriate vector, and screened with the F12 probe. Cloned DNA is mapped to determine if regions contiguous to the F12 region are present on the inserted DNA identified by homology to the F12 region. The contiguous DNA is sequenced, and tested for specificity and sensitivity as a probe for the detection of *E. coli* O157:H7.

The nucleotide length of the probe is chosen using customary criterion. Ten nucleotides is generally the lower limit for such nucleotide segments, because sequences smaller than that sometimes fail to form stable hybrid duplexes, or may hybridize nonspecifically with unrelated genes that happen to share short stretches of complementary sequence with the desired target sequence. Accordingly, in preferred embodiments, the probes are at least 10 nucleotides in length, with the oligonucleotide being capable of forming a detectable stable duplex with the F12 region sequence(s). More preferred are probes of at least 15 nucleotides, as such probes are more likely to form stable duplexes with their complementary sequences. Oligonucleotides at least 15 bases long are very likely to be specific, as sequences of this length will occur by chance no more than once in a mammalian genome, hence are extremely unlikely to occur by chance in a bacterial genome. Preferred probes will range from 15 to 50 bases in length, as probes in this range can be prepared at a reasonable cost using commercially available DNA synthesizers or services that synthesize oligonucleotides on request. The invention also contemplates that fragments of DNA even longer than 50 nucleotides may be obtained from the F12 region, by using restriction endonucleases, or by using PCR primers and subsequently cloning these longer fragments.

For use in the described selection system or for analyzing food or fecal samples, probes must be labeled in order to be detectable in hybrids formed during the assays. Synthetic probes are conventionally labeled with radioactive phosphorus using polynucleotide kinase. Alternatively the probes can be tagged with an affinity reagent such as biotin or streptavidin, thus enabling the probe to bind to an enzyme capable of cleaving a chromogenic substrate (for details, see Sambrook et al.).

Various conventional protocols can be employed for the hybridization step. Generally, the labeled probe is present in a suitable hybridization solution, while the target nucleic acids are fixed to an insoluble substratum, such as derivatized nylon. In the preferred embodiment, target DNA sequences and labeled probes are incubated under stringent hybridization conditions. Such conditions are generally understood to be those that permit only perfectly matched or nearly perfectly matched hybrids to form, and their use will assure that probes hybridize specifically with sequences of *E. coli* O157:H7. The destabilizing effects of mismatched bases increases as probe length decreases, such that for probes shorter than 20 nucleotides, stringent hybridization conditions will rarely tolerate any mismatched bases. For longer probes, it is possible that a few mismatches may be present in hybrids that form even under stringent conditions. In some situations, practitioners could be misled by results involving mismatched hybrids, but in the present instance, the screening methods provided ensure identification of probes having the appropriate specificity regardless of whether mismatches may be present. That is, the screening procedure identifies probes that react with the targeted O157:H7 strain (and, optimally, with the positive control F 12 region) but not with the negative control bacteria. Hence it is immaterial whether any given probe forms a perfect or only a near-perfect hybrid, as the ability to distinguish these two groups of bacteria is the only pertinent quality in the context of the present test assays.

A variety of operable hybridization conditions are available to one skilled in the art, e.g., as provided in Sambrook et al. For probes longer than about 200 nucleotides in length, hybridization usually is carried out at about 25° C. below the melting temperature of the hybrid, as this gives the optimal rate of duplex formation. For shorter probes, hybridization is usually carried out closer to the calculated melting temperature of a perfect hybrid, e.g., 10°–15° C. below the melting temperature. For probes of various lengths, melting temperatures for perfectly matched hybrids can be determined empirically, or can be calculated using one of the formulas found in Sambrook et at. An exemplary hybridization solution for oligonucleotides contains 6 X SSC (ca. 1M [Na+]), and 0.5% sodium dodecyl sulfate.

The subject sequences can also be used for detection of *E. coli* O157:H7 in polymicrobial samples using polymerase chain reaction (PCR) methodology. For example, nucleotide primers which have a high likelihood of being specific for *E. coli* O157:H7 are determined, using techniques described above, and used in PCR assays to detect genomic sequences specific for *E. coli* O157:H7 in enrichment cultures likely to contain the target organism. For example, a sample suspected of having *E. coli* O157:H7 in its natural condition (e.g., ground meat or bovine feces) is incubated in a broth enrichment culture, DNA is extracted using standard techniques, the DNA is annealed to the appropriate primers, in the PCR reaction, and the resulting bands are examined on agarose gels for products of this reaction. A positive band suggests the presence of *E. coli* O157:H7. It is estimated that such a technique could be performed within several hours of the start of incubation, that is, in a time period considerably less than present techniques which rely on amplification of the organism to an extent that antigens can be detected.

In another embodiment, the expression products (SEQ IDS NO:5 and NO:6, respectively) of the nucleotide sequences shown in SEQ ID NOS: 2 and 3 are considered candidate immunogens for preparing antibody reagents for detection of the O157:H7 strain.

The invention is further illustrated by the following example, which describes detection of *E. coli* O157:H7 using a nucleic acid probe (SEQ ID NO:4) encompassing the disclosed rfbE homologous sequence (SEQ ID NO:3).

EXAMPLE

Total bacterial DNA (chromosome and plasmid) was prepared from a variety of bacteria, including: *E. coli* O157:H7 strain 86–24, a strain which caused an outbreak of infection in a fast food restaurant in Walla Walla, Wash., in 1986 (Griffin et al., Annals of Internal Medicine, 109:705–712, 1988) as the positive control (the F12 region was derived from this strain); *E. coli* NM544 (a laboratory strain) as the negative control (Raleigh et al., Nucleic Acids Research, 16:1563–1575, 1988); five test strains from diarrheal *E. coli* group 5 (all *E. coli* O55:H7); a clone of *E. coli* which is closely related to *E. coli* O157:H7 (Whittam et al., Infection and Immunity, 61:1619–1629, 1993); and five test strains or *E. coli* O157:H43. The DNA from each of these organisms was digested with EcoRI, separated electrophoretically in 0.7% agarose, and transferred to a nylon support membrane. The immobilized DNA was probed with a fragment of F12 DNA (SEQ ID NO:4), and homologous DNA sequences were detected in: *E. coli* O157:H7 strain 86–24; and four of the five *E. coli* O157:H43 strains probed, though at lesser intensity. This probe (SEQ ID NO:4) identified an EcoRI fragment of ca. 6 kb in the strains which were positive. The probe did not identify homologous DNA in the negative control, the *E. coli* O55:H7 strains, and one of the *E. coli* O157:H43 strains. It is important to note, however, that the nonreactive *E. coli* O157:H43 strain was only very weakly positive in the Oxoid latex particle agglutination test (unlike the other *E. coli* O157:H43 strains), and its identity as a member of the O157 serogroup is not certain.

Plasmid pF12 containing SEQ ID NO:7 (i.e., nucleotides 32-2199 of SEQ ID NO:1) was deposited on Apr. 14, 1995, at the American Type Culture Collection, 12301 Parklawn Drive, Rockville, Md. 20852, U.S.A. pF12 is a PCR product of the cloned homologs of the *V. cholerae* rfbE gene and the gene encoding the putative transmembrane export protein of *Y. pseudotuberculosis* from *E. coli* O157:H7 strain 86-24, as well as some flanking sequence. It was cloned by using as primers the sequences 5'CTT CTG GCA TGA TTG ATT GGC3' (SEQ ID NO:8) and 3'CGA GTG GGG CGG TGG AAT TG5' (SEQ ID NO:9) from the deduced nucleotide sequences of the cloned DNA segments surrounding the TripboA insertion in strain F12. The primers were modified to contain BamHI and EcoRI sites, respectively, which were used to insert the PCK product into pSK+ (Stratagene) at these sites. Confirmatory sequencing from the PCR products and of the cloned regions flanking the TnphoA insertion demonstrate two errors in these cloned segments. (SEQ ID NO:1 is the correct sequence.) These include a T at position 964 (which is an erroneous C in the cloned insert deposited at ATCC) and a C at position 1510 (which is an erroneous T in the cloned insert deposited at ATCC).

The practice of the present invention will employ, unless otherwise indicated, a number of conventional techniques of molecular and cellular biology, recombinant DNA, microbiology, and immunology, which are within the skill of the art. Such techniques are explained fully in the scientific literature and detailed experimental protocols are available in a number of technical manuals; see for example: F. M. Ausubel et al. (eds.), "Current Protocols in Molecular Biology," (1987 and 1993); Kriegler, M. (ed.), "Gene Transfer and Expression, a Laboratory Manual," (1990), W. H. Freeman Publishers; Sambrook, Fritsch, and Maniatis, "Molecular Cloning: A Laboratory Manual," Second Edition (1989); Erlich, H. A. (ed.) "PCR Technology: Principles and Applications for DNA Amplification," (1989), Stockton Press; Langone, J. J. and H. Van Vunakis (eds.), "Immunological Techniques, Part I: Hybridoma technology and monoclonal antibodies," Methods in Enzymology 121:1–947 (1986); Hurrell, J. G. R. (ed.), "Monoclonal Hybridoma Antibodies: Techniques and Applications," (1982), CRC Press, Boca Raton, Fla.; Coligan, J. E. et al. (eds), "Current Protocols in Immunology," (1991), Greene Publishing and Wiley-Interscience, N.Y.; Weir, D. M., "Handbook of Experimental Immunology," (1986), Blackwell Scientific; Kurstack, E., "Enzyme Immunodiagnostics," (1986), Academic Press, San Diego; Polak, J. M. and S. Van Noorden (eds.), "Immunocytochemistry: Practical Applications in Pathology and Biology," (1983), John Wright PSG, Littleton, Mass.; Sternberger, L. A., "Immunocytochemistry," (1986), Wiley, N.Y.; and primary references cited therein. All publications, patents, and patent publications mentioned herein are hereby incorporated herein by reference in their entirety.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. An isolated nucleic acid molecule that consists of at least 15 contiguous nucleotides of SEQ ID NO:1 or its exact complement.

2. A nucleic acid probe for detecting the presence of enterohemorrhagic *E. coli* O157:H7, consisting of isolated nucleic acid molecule at least 15 nucleotides in length, said isolated nucleic acid molecule hybridizing under stringent conditions to SEQ ID NO:1 or its exact complement and to the DNA of *E. coli* O157:H7 but not to the DNA of enteropathogenic *E. coli* O55:H7.

* * * * *

UNITED STATES PATENT AND TRADEMARK OFFICE
CERTIFICATE OF CORRECTION

PATENT NO. : 5,654,417  
DATED : August 5, 1997  
INVENTOR(S) : P.I. Tarr et al.

Page 1 of 2

It is certified that error appears in the above-indentified patent and that said Letters Patent is hereby corrected as shown below:

| COLUMN | LINE | |
|---|---|---|
| Pg. 1, col. 2 | Assistant Examiner | After "Whisenant" insert --, Ph.D.-- |
| 1 | 56 | "*E. hermnaii*" should read --*E. hermanii*-- |
| 2 | 15 | "58: 1764" should read --58:1746-- |
| 2 | 28 | "et at." should read --et al.-- |
| 2 | 28 | "Journal of infectious" should read --Journal of Infectious-- |
| 3 | 2 | "et ai." should read --et al.-- |
| 3 | 2 | "Acad. Sci," should read --Acad. Sci.-- |
| 3 | 14 | "*E. coil*" should read --*E. coli*-- |
| 3 | 24 | "*E. coil*" should read --*E. coli*-- |
| 3 | 28 | "nudeic acid" should read --nucleic acid-- |
| 3 | 30 | "flames" should read --frames-- |
| 3 | 52 | "dosely" should read --closely-- |
| 3 | 55 | "dosest" should read --closest-- |
| 4 | 10 | "et at." should read --et al.-- |
| 5 | 3 | "polynucleofide" should read --polynucleotide-- |
| 5 | 6 | "chromogenie" should read --chromogenic-- |
| 5 | 45 | "et at." should read --et al.-- |

UNITED STATES PATENT AND TRADEMARK OFFICE
CERTIFICATE OF CORRECTION

PATENT NO. : 5,654,417
DATED : August 5, 1997
INVENTOR(S) : P.I. Tarr et al.

It is certified that error appears in the above-indentified patent and that said Letters Patent is hereby corrected as shown below:

| COLUMN | LINE | |
|---|---|---|
| 5 | 51 | "0157:H7" should read --O157:H7-- |
| 6 | 22 | "*O*157:H7" should read --O157:H7-- |
| 6 | 24 | "strains or *E. coli*" should read --strains of *E. coli*-- |
| 6 | 54 | "PCK" should read --PCR-- |
| 7 | 3 | "et at." should read --et al.-- |
| 8 | 7 | "Stemberger, L." should read --Sternberger, L.-- |

Signed and Sealed this

Thirteenth Day of January, 1998

Attest:

BRUCE LEHMAN

*Attesting Officer*      *Commissioner of Patents and Trademarks*